(12) United States Patent
Smith

(10) Patent No.: US 7,704,532 B1
(45) Date of Patent: Apr. 27, 2010

(54) METHOD FOR ALTERING ALLERGENIC PROTEIN IN THE ENVIRONMENT

(76) Inventor: C. Steven Smith, 125 Promenade Ct., Louisville, KY (US) 40223

( * ) Notice: Subject to any disclaimer, the term of this patent is extended or adjusted under 35 U.S.C. 154(b) by 34 days.

(21) Appl. No.: 11/223,554

(22) Filed: Sep. 9, 2005

Related U.S. Application Data

(63) Continuation of application No. 10/194,596, filed on Jul. 11, 2002, now abandoned.

(60) Provisional application No. 60/304,722, filed on Jul. 11, 2001.

(51) Int. Cl.
*A61K 33/06* (2006.01)
(52) U.S. Cl. .................... 424/682; 424/810
(58) Field of Classification Search .......... 424/682, 424/678, 681, 810
See application file for complete search history.

(56) References Cited

U.S. PATENT DOCUMENTS

| | | | |
|---|---|---|---|
| 4,806,526 | A | 2/1989 | Green |
| 4,977,142 | A | 12/1990 | Green |
| 5,192,449 | A | 3/1993 | Huang et al. |
| 5,254,238 | A | 10/1993 | Ishii et al. |
| 5,266,473 | A | 11/1993 | Nielsen |
| 5,688,532 | A | 11/1997 | Bryce-Smith |
| 5,916,917 | A | 6/1999 | Suh et al. |
| 6,037,358 | A | 3/2000 | Gordziel |
| 6,300,326 | B1 | 10/2001 | Dobbs et al. |
| 6,830,764 | B2 | 12/2004 | Inui et al. |
| 2002/0061281 | A1 | 5/2002 | Osbakken et al. |
| 2002/0150540 | A1* | 10/2002 | Yoshikawa et al. ............ 424/43 |
| 2003/0070674 | A1 | 4/2003 | Perry et al. |
| 2003/0206965 | A1 | 11/2003 | Hasan et al. |

FOREIGN PATENT DOCUMENTS

| | | |
|---|---|---|
| EP | 0217975 | 4/1987 |
| GB | 2 329 586 | 3/1999 |
| GB | 2 329 587 | 3/1999 |
| WO | WO 02/062354 | 8/2002 |

OTHER PUBLICATIONS

Remington's Pharmaceutical Sciences (17th Ed. 1985), pp. 1396,1397.*
Smith et al., Aluminum sulfate significantly reduces the skin test response to common allergens in sensitized patients, Clinical and Molecular Allergy (2006), 4:1 [online], [retrieved on Dec. 23, 2007]. Retrieved from the Internet <URL: http://www.clinicalmolecularallergy.com/content/4/1/1>.*
Aalberse, "Structural biology of allergens," Journal of Allergy & Clinical Immunology, Aug. 2000, vol. 106(2), pp. 228-238, downloaded Sep. 11, 2003 at http://gateway1.ovid.com/ovidweb.cgi.
Baker et al., "Identification of some rabgit allergens as lipocalins," Clinical and Experimental Allergy, 2001, vol. 31, pp. 303-312.
Ball et al, "A major continuous allergenic epitope of bovine beta-lactoglobulin recognized by human IgE binding," Clinical and Experimental, 1994, vol. 24, pp. 758-764.
Custovic et al., "Controlling indoor allergens," Annals of Allergy, Asthma, & Immunology, 2002, vol. 88, pp. 432-441.
De Groot et al., "Affinity purification of a major and a minor allergen from dog extract: Sserologic activity of affinity-purified Can f I and of Can f 1-depleted extract," Journal of Allergy Clinical Immunology, 1990, vol. 87 No. 6, pp. 1056-1065.
Ellenhorn et al., Medical Toxicology: Diagnosis and Treatment of Human Poisoning, 1988, Chapter 37, pp. 1009-1011.
Virtanen, "Lipocalin allergens," Allergy, 2001, vol. 56: Suppl. 67, pp. 48-51.
Kauppinen et al., "Mutant derivatives of the main respiratory allergen of cows are less allergenic than the intact molecule," Clinical and Experimental Allergy, 1999, vol. 29, pp. 989-996.
Konieczny et al., "The major dog allergens, Can f1 and Can f2, are salivary lipocalin proteins: cloning and immunological characterization of the recombinant forms," Immunology, 1997, vol. 92, pp. 577-586.

(Continued)

*Primary Examiner*—Johann R Richter
*Assistant Examiner*—Andriae M Holt
(74) *Attorney, Agent, or Firm*—Stites & Harbison PLLC; Mandy Wilson Decker

(57) ABSTRACT

Described are compositions and methods for use thereof for prevention or mitigation of allergic reactions in humans and animals. Novel compositions comprised of, e.g., an acidic salt solution of aluminum, calcium or magnesium, are provided for topical or contact application to physically and/or chemically alter an allergenic protein present in the environment and thereby lower the allergenicity of the protein. The compositions of the invention, e.g., comprised of aluminum sulfate, can be used to deactivate many types of proteinaceous allergens such as dust mite and cockroach body dust, animal dander, dried saliva, mold spore antigens, airborne pollen protein and the like. Compositions can be applied on an as needed basis to a wide variety of surfaces, interiors, furniture, pet bedding, plants and the like. The compositions provided may also be utilized to mitigate allergens present on clothing, e.g., for use in commercial dry cleaning or in household laundry applications.

9 Claims, 4 Drawing Sheets

OTHER PUBLICATIONS

Liccardi et al., "Pets and cockroaches: two increasing causes of respiratory allergy in indoor environments. Characteristics of airways sensitization and prevention strategies," Respiratory Medicine, 2000, vol. 94, pp. 1109-1118, Harcourt Publishers Ltd.

Lorusso et al., "Immunologic and biochemical properties of the major mouse urinary allergen (Mus m I)," Journal of Allergy and Clinical Immunology, 1986, vol. 78, No. 5, Part 1, pp. 928-937.

Rush et al., "Treatment of Inflammatory Airway Disease: Aerosol Delivery Devices and Medications," AAEP Proceedings, 2002, vol. 48, pp. 218-227.

U. S. Center for Disease Control, "Forecasted State-Specific Estimates of Self-Reported Asthma Prevalence—United States, 1998," Dec. 4, 1998, vol. 47, pp. 1022-1025.

* cited by examiner

METHOD FOR ALTERING ALLERGENIC PROTEIN IN THE ENVIRONMENT

CROSS REFERENCES TO RELATED APPLICATIONS

This application claims priority from U.S. Provisional Application Ser. No. 60/304,722 filed Jul. 11, 2001, and is a continuation of U.S. patent application Ser. No. 10/194,596 filed Jul. 11, 2002 now abandoned. The entire disclosures contained in U.S. Provisional Application Ser. No. 60/304,722 and U.S. application Ser. No. 10/194,596 are incorporated herein by this reference.

FIELD OF THE INVENTION

The present invention generally relates to the prevention or material mitigation of allergic reactions in humans (and other susceptible animals). In particular, the present invention relates to a novel composition, e.g., comprised of salts of aluminum, calcium and/or magnesium in a water or buffer solution and to the methods of use thereof to alter selected proteins that constitute allergens (or antigens) and thereby to lower their ability to cause allergic reactions in susceptible humans (and/or in other susceptible animals, e.g., in household pets or other companion and/or production animals).

BACKGROUND OF THE INVENTION

One critical function of the human (and animal) immune system is to assess whether a physical particle entering the body is a friend or foe. Occasionally for some people (and animals) and frequently or continuously for others, the immune system wrongly identifies an otherwise harmless particle as foe—acting as if the particle were a dangerous, infectious microorganism. The overtly harmless particle may be, e.g., a molecule of pollen, or dog dander, or cat saliva or any of a host of other proteins we know to be allergens, i.e., antigens that trigger an adverse immune system response in susceptible humans (and susceptible animals). Chromosomal characteristics seem to determine which members of any given population will "have allergies"; estimates of the United States population are that at least 20% and as many as 30% are atopic, i.e., they produce abnormal IgE and/or abnormal amounts of IgE, and thus develop hypersensitivity to allergens.

Asthma, rhinitis, eczema, urticaria, sinusitis and conjunctivitis all may be clinical signs of allergic reactions to environmental allergens. These clinical signs are associated with the immune system's release of histamine and other cytokines and their effects on the human body. This histamine-led, multiple cytokine cascade is triggered by the immune system's response to multiple, ubiquitous environmental allergens.

The currently recognized methods for dealing with allergies and allergy-based extrinsic asthma in humans (and animals) are: (i) avoidance of the source of the triggering allergen(s); (ii) pharmacotherapy; and (iii) immunotherapy. The first line of defense for allergic individuals is controlling their environment. Although initiating this control in public facilities can be difficult or even impossible, the allergic individual can largely protect his own home from allergy-producing antigens with the proper information. Allergists emphasize, through patient education, the need to remove or reduce from the residential environment allergen-producing sources, e.g., dogs, cats, dust mites, mold, cockroaches, indoor-flora and other sources. For physicians specializing in allergy, asthma and immunology, the control of the source of antigens in the home has historically taken precedence over treatment through immunotherapy or pharmacotherapy.

Pharmacotherapy includes a myriad of over-the-counter medications and prescription drugs designed to reduce the effects of the histamine response to allergens (antihistamines). These formulations relieve some clinical symptoms (in 40-50% of patients) but in no way "cure" the patient. Quite unlike immunotherapy, no permanent changes are evoked by pharmacotherapy-only brief respites from allergic symptoms.

When allergy symptoms persist despite encouragement of patients to avoid the source of allergens or to use medications, allergists suggest the introduction of immunotherapy in the form of allergy injections. Over time, the injections hyposensitize the patients. Ever increasing amounts of specific allergens are periodically introduced to the immune system. This eventually significantly reduces the scope and intensity of the cytokine response and thereby reduces the occurrence of allergic symptoms.

The "avoidance" method raises fairness, ethical and practical issues for an allergic patient and those with whom he lives. One could question whether a child's mild allergy to pets should cause, say, three other children and two adults to have to live without the salutary emotional benefits of living with two dogs and a cat that, themselves, have been "members of the family" for many years. Likewise one may question whether mold and pollen allergies for one member of an extended family should mean that twenty other members cannot have a large, cut, live Christmas tree for their annual two-day celebration at Grandmother's house. Likewise, an allergy to horse dander could mean that an annual three-day ride with friends will lose a key participant.

Equally problematic for the allergy sufferer are the costs and side effects of pharmacotherapy. Similarly, the cost and inconvenience of weekly or twice-weekly trips to a physician's office for immunotherapy injections can be overwhelming.

Given these shortcomings of the prevailing modalities of dealing with allergies, another modality-one that permits pets to remain in the home, that allows houseplants and Christmas trees to be natural-would be welcome and helpful to literally millions of allergy patients and those with whom they interact. Accordingly, there is a need in the art for such a modality.

Moreover, increasing evidence confirms that allergies can lead to more severe consequences. Thus, there is especially a need in the art for a modality that can mitigate the effects of allergens that are difficult, if not impossible to remove from the environment. For example, cockroach and rodent dander and urine can lead to pediatric asthma among inner city housing project residents. A modality for dealing with these difficult to eliminate allergens in the indoor environment would have lasting health benefits. The benefits are especially compelling in regard to a substantial disadvantaged population, one that cannot be reasonably expected to bear the cost of, and display the required discipline for, pharmacotherapy or immunotherapy.

With: (i) allergies as the number one cause of missed work; and (ii) asthma the number one cause both of missed school and childhood hospitalization; any effective additive modality in mitigation of the allergic response has an important role to play.

SUMMARY OF THE INVENTION

The present invention provides a method of prevention or material mitigation of allergic reactions in humans (and susceptible pets). In particular, the present invention relates to a novel composition comprised of salts of aluminum, calcium and/or magnesium in a suitable delivery system or vehicle, e.g., a water-based and/or a buffered solution, and to the methods of use thereof to alter, e.g., in the indoor environment, the proteins that constitute allergens to lower their allergenicity. This in turn, relieves the clinical effects of the cytokine cascade.

One embodiment of the invention provides a novel composition comprised of aluminum sulfate, stabilizers, adjuvants and water. In a preferred embodiment, e.g., in a formulation adapted for sponge, blot or spray application, the composition can comprise from between about a 1.0% to about a 30.0% solution of aluminum sulfate. This formulation can be used to deactivate many types of proteinaceous allergens including, but not limited to, dust mite and cockroach body dust, animal danders and dried saliva, mold spore antigens and airborne pollen protein allergens and the like.

A presently preferred embodiment of the invention provides a novel composition comprised of aluminum sulfate, stabilizers and adjuvants in water that is adapted for periodical topical administration on an as needed basis to a wide variety of surfaces, e.g., floor coverings, walls bedding, window coverings, vehicle (e.g., automobile) interiors, furniture, pet bedding, plants (e.g., household plants) and the like. The compositions of the invention may also be utilized to mitigate allergens present on clothing, e.g., for use in commercial dry cleaning or in household laundry applications such as an additive, e.g., a fabric or other laundry sheet impregnated with the composition e.g., for treatment of clothes as they tumble in the dryer.

An additional embodiment of the invention provides a novel composition for the continual alteration of allergens on the coats of pets. In one embodiment, this formulation is comprised of at least one aluminum salt and is adapted to a wet-wipe, bath, rinse or spray formulation for use on animals, e.g., pets and companion animals which include, but are not limited to, e.g., dogs, cats, and horses. The present invention also provides a novel composition that is adapted to, deliver the active ingredients in a time-release manner, for a longer-acting formulation for delivery into various environmental areas.

The present invention further provides methods for the dispensing of active ingredients onto other areas of the indoor environment not specifically identified above, including, e.g., heating, ventilating and air conditioning duct work and filtration units, public transportation and other vehicle interiors such as aircraft seats and air filtration systems and trains, public housing structures and other indoor places of public accommodation.

DETAILED DESCRIPTION OF THE INVENTION

Figure 1:
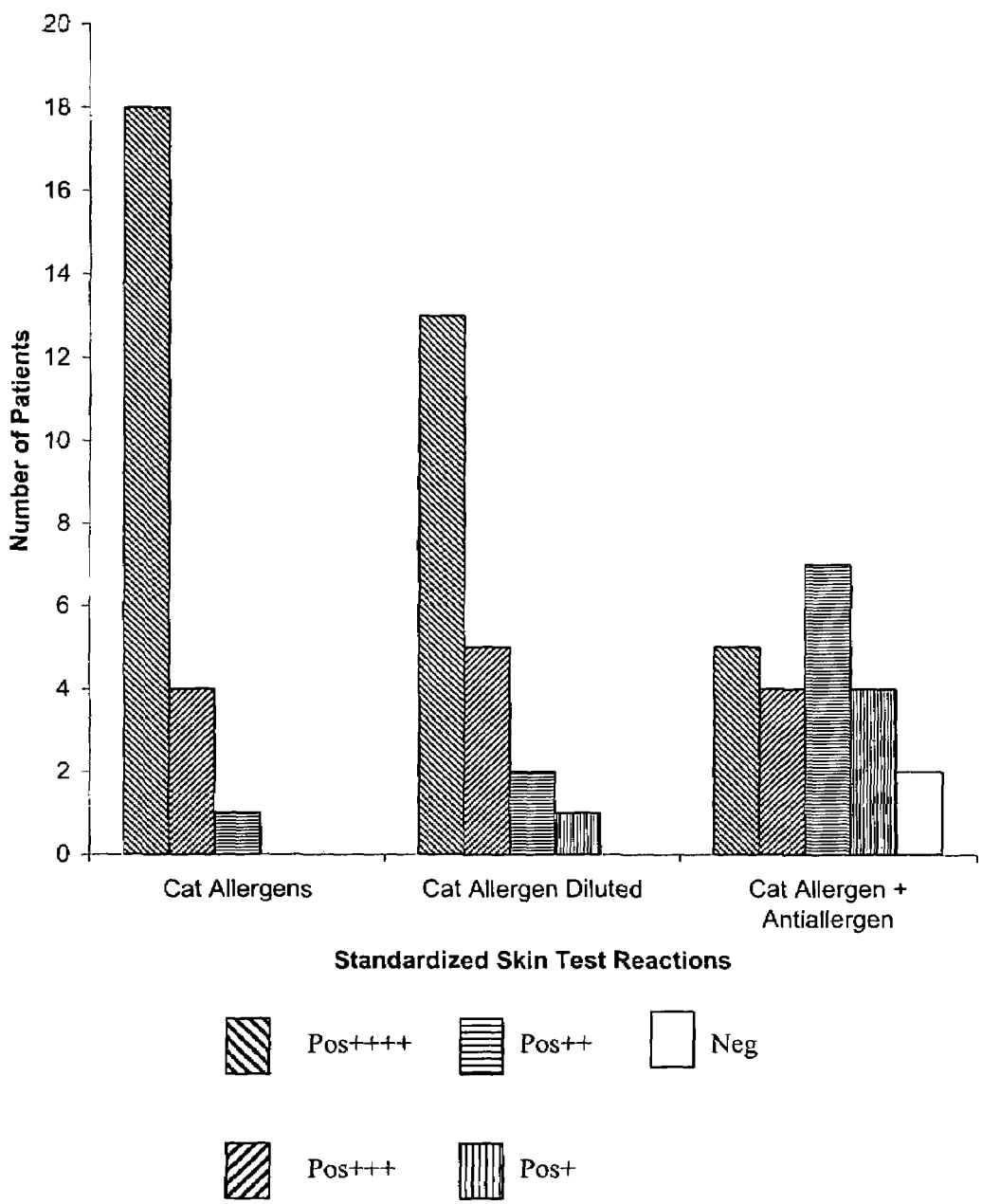
FIG. 1 is a bar graph comparing relative response to cat allergen, a cat allergen control, and cat allergen treated with a composition comprised of aluminum sulfate (antiallergen).
Figure 2:
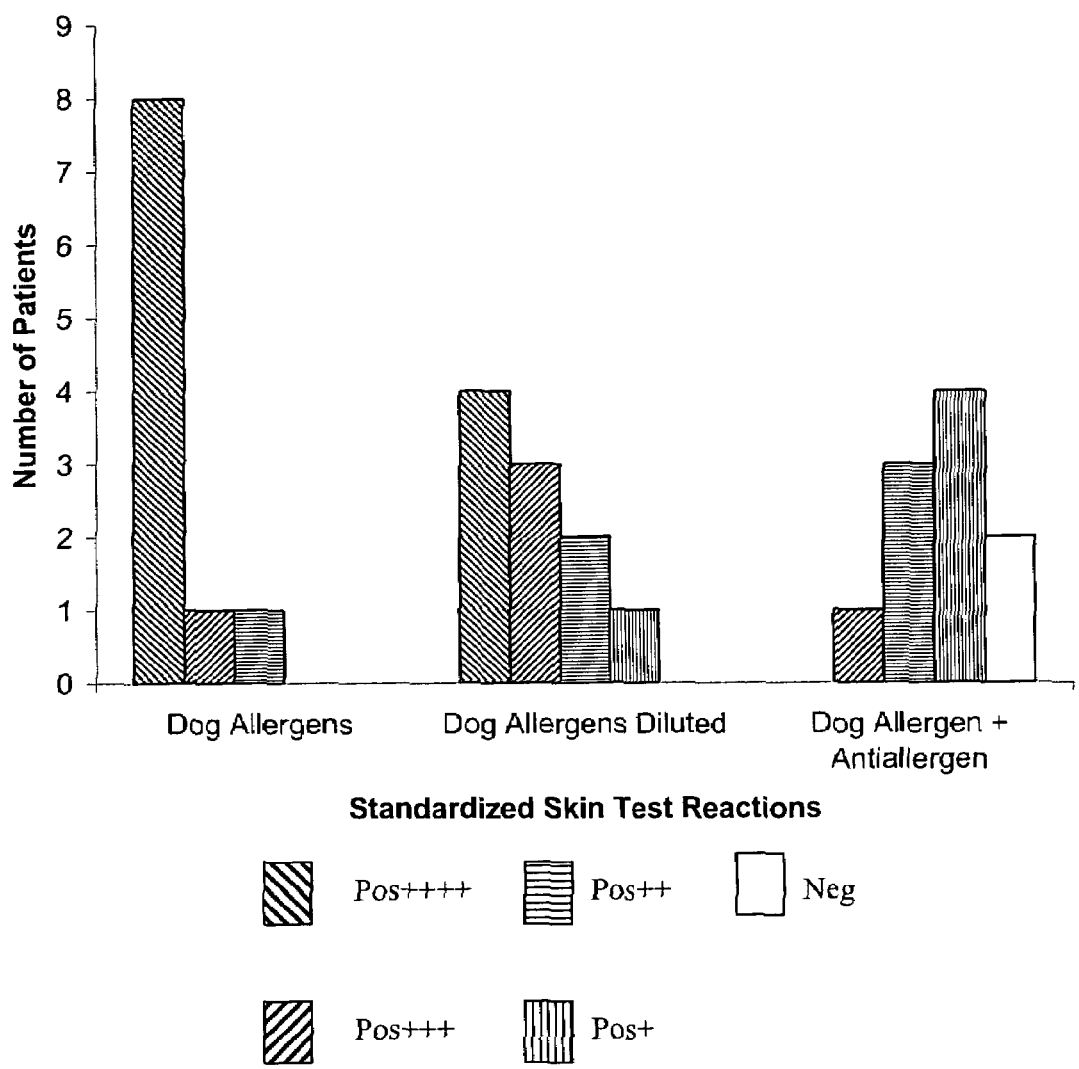
FIG. 2 is a bar graph comparing relative response to dog allergen, a dog allergen control, and dog allergen treated with a composition comprised of aluminum sulfate (antiallergen).
Figure 3:
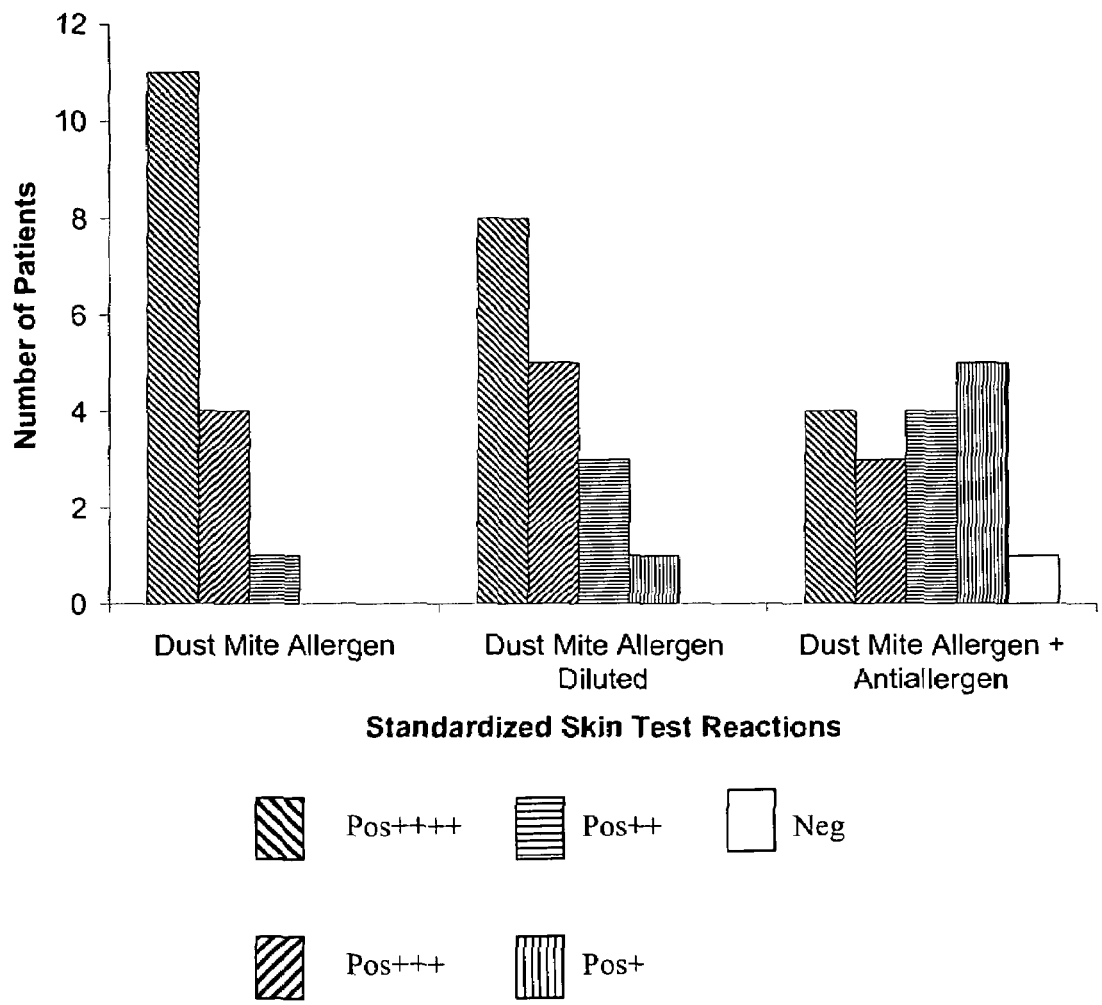
FIG. 3 is a bar graph comparing relative response to dust mite fecal particle allergen, a dust mite fecal particle allergen control, and dust mite fecal particle allergen treated with a composition comprised of aluminum sulfate.
Figure 4:
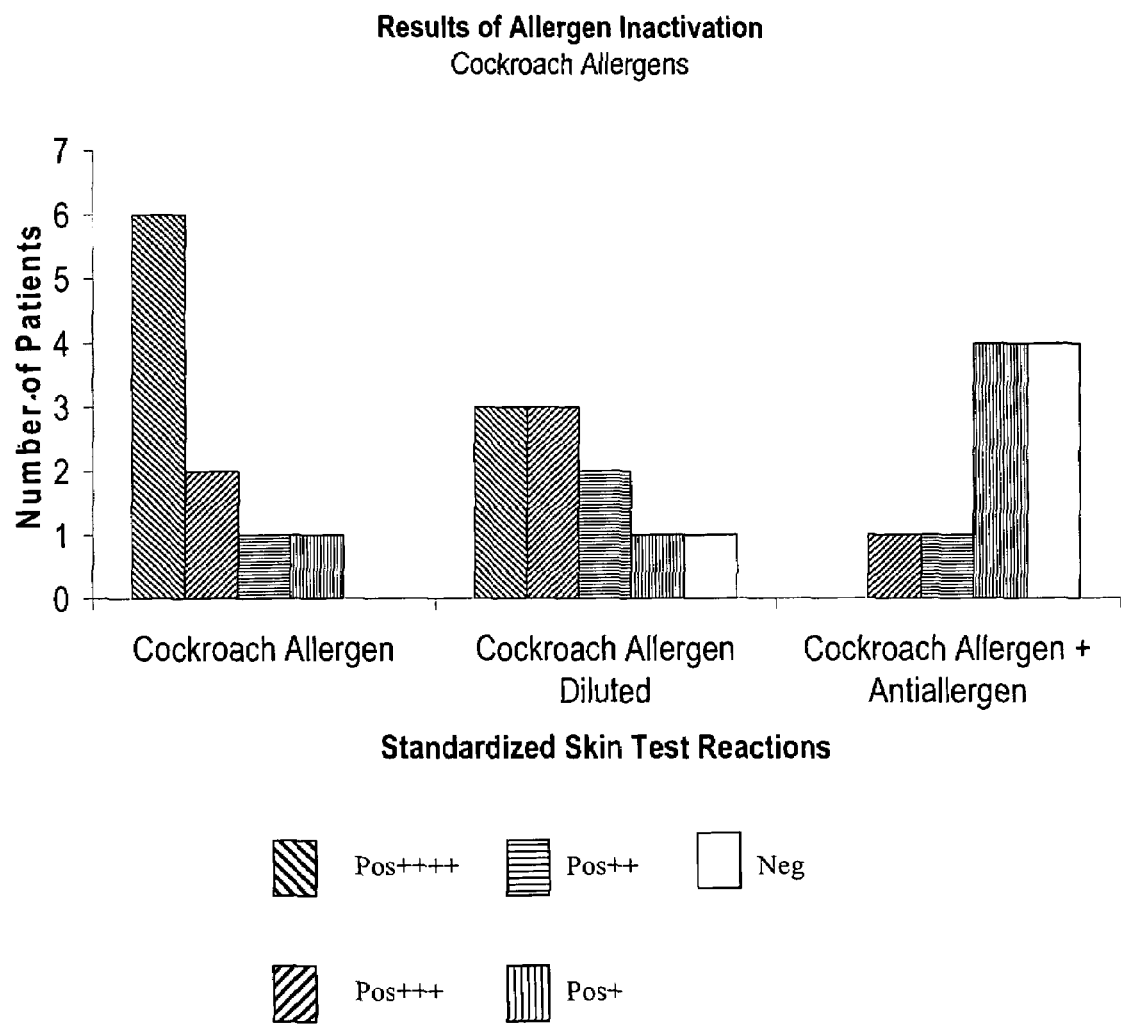
FIG. 4 is a bar graph comparing relative response to cockroach allergen, a cockroach allergen control, and cockroach allergen treated with a composition comprised of aluminum sulfate (antiallergen).

The present invention provides a method of prevention or mitigation of allergic reactions in humans and in animals, e.g., in susceptible companion animals). In particular, the present invention relates to a novel composition comprised of an acidic salt solution and to the methods of use thereof to sufficiently alter allergens in our environment to lower their allergenicity. The invention incorporates the contemplation that the compositions of the invention can consist of any of the class of soluble salts including but not limited to aluminum, magnesium, or calcium that have an acidic pH when dissolved in water with or without buffer. Applied compositions of the invention reduce the volume of free allergens thereby reducing the symptoms of allergic patients encountering the treated environment.

Examples of suitable salts for use in the compositions of the invention include, but are not limited to aluminum sulfate, aluminum nitrate, aluminum chloride, calcium sulfate, calcium nitrate, calcium chloride, magnesium sulfate, magnesium nitrate, and magnesium chloride. These salts can be used alone or in combination in the compositions provided herein and may further be combined with stabilizers, adjuvants and/or biological growth inhibitors and delivery vehicle modifiers such as a surfactant. As can be appreciated by one of skill in the art, the compositions provide by the invention can be formulated for various delivery systems.

In a presently preferred embodiment, the composition of the invention is comprised of aluminum sulfate and a suitable solvent. As set forth above, the solvent can be any suitable solvent, including, but not limited to, e.g., water or a citrate buffer. Specific formulations of the compositions of the invention can include powders, gels, ointments, creams, solutions, suspensions, sustained release preparations, patches, wet-wipes, aerosols and the like.

One of skill in the art can appreciate that, depending upon the site to be protected, the concentration of the compositions of the invention can vary and the treatment regimen can be optimized by methods known in the art. The compositions for administration can comprise from about 1% to 30% final concentration of the active, a dry formulation to be mixed in situ, and further formulated for both single dosage, daily, weekly and monthly applications, and precise concentration/area.

For example, one embodiment of the invention provides a composition comprised of aluminum sulfate and water. In a formulation adapted for spray application, the composition can comprise about a 7% solution of the active, aluminum sulfate. This formulation can be used to alter allergens including but not limited to, e.g., dust mite allergens and cockroach allergens.

In another embodiment, the compositions of the invention are comprised of aluminum sulfate in water and can be adapted for topical administration daily, weekly, or monthly on a wide variety of surfaces where allergenic proteins may be found, e.g., floor coverings, bedding, window coverings, vehicle interiors and the like.

For example, the currently preferred treatment regimen of the administration of the compositions provided herein for use on allergic surfaces comprises administration of a composition comprised of between about 5% and about 10% of aluminum sulfate in solution, but especially about 7% aluminum sulfate.

In one embodiment, the invention provides a composition comprised of at least one aluminum salt that is adapted to a wet-wipe formulation for use on animals, e.g., pets, including but not limited to dogs, cats and horses. These formulations are suitable for dispensing directly onto the animal's coat.

In the presently preferred topical embodiment wherein the compositions of the invention are adapted for localized topical delivery, the composition can comprise from about 5% to about 10% but especially about 7-8% of the active for effective use.

The invention also provides compositions formulated with at least one release agent that is capable of delivering the compositions of the invention to large surfaces, including but not limited to, e.g., carpets, floor boards, walls, cabinets and stall bedding and the like. Such compositions preferably are comprised of at least one of the aforementioned salts adapted for timed release or timed efficacy in the environment.

While not wishing to be bound by any particular theory or construct, by way of example, the compositions of the invention can be used for direct application to any surface where antigenic material may exist. The compositions, once applied, contact the antigen, e.g, an antigenic protein, and function to alter the antigenic characteristics of the protein to thereby reduce antigenticity in a selected individual. Alteration of the antigenic characteristics of the antigen is meant to include any alteration, both physical and/or chemical alteration such that the antigen is rendered less antigenic (produces a reduced immune response in the selected individual, e.g., a human).

In a presently preferred embodiment, for example, a composition comprised of an effective amount of aluminum sulfate can be applied to a surface containing antigenic material, e.g. a protein such as cat hair. The aluminum sulfate contacts the antigenic material and alters antigenicity, e.g., by altering the physical and/or chemical properties of the antigen, e.g., by denaturing at least a portion of the protein.

Antigenic (or allergenic) proteins, just like all proteins, have specific structures. These structures are necessary for the protein's ability to carry out its function. In the case of allergenic proteins, the structure contains a specific binding site or epitope that is necessary to bind to IgE and trigger the allergenic reaction. The binding site or epitope on the allergenic protein is the only part of the protein that requires alteration to change or alter the protein's level of antigenicity. This antigenic site, or epitope has been located in the known structures of many allergens, such as protein derived from the cat, dog, horse, and cockroach. In one embodiment, the method of action of the compositions of the invention, e.g., the salt solutions, e.g., aluminum sulfate, is the denaturation or partial denaturation of the allergenic protein.

As can be appreciated by one of skill in the art, there are many levels of denaturation, ranging from a slight change in the protein to a total destruction of the protein. As provided by the teachings herein, the moderate denaturation allowed by an acidic salt solutions, e.g., aluminum sulfate, changes the three-dimensional structure of the allergenic protein at the binding site or epitope. Proteins are held together by molecular bonds, which are the most difficult to break, and other forces such as hydrogen bonding, salt bridges and other forces that maintain the protein's three-dimensional structure. In the moderate denaturation of the allergenic proteins it is often the hydrogen bonding and salt bridges that are disturbed or altered, allowing for movement in the protein, and therefore an alteration in the three-dimensional structure. Aluminum sulfate, for example, contacts the antigenic material and alters antigenicity, e.g., by denaturing, that is altering the bonding in the structure of the protein, which in turn alters the chemical capabilities of the antigen protein e.g. binding and thereby reduces or alleviates the antigenicity of the protein.

Example

A clinical trial of 39 subjects of proven allergic status was accomplished to confirm the viability and efficacy of the present invention. The subjects were evaluated using skin prick testing with skin test antigens, including a cat allergen, a dog allergen, dust mite fecal particle allergen, and cockroach allergens modified in the above manner common to their treatment.

The allergens that were used in the clinical trials were supplied by Greer Laboratories, Inc. of Lenoir, N.C. The cat allergens were Greer Laboratories, Standardized Cat Hair Extract. The cat allergens are composed of extracts of cat pelt and cat dander standardized by comparing potency in cat allergen 1 (*Felis domesticus* 1) (Fel d 1) units measured by radial immunodiffusion against a reference standard from the Center for Biologics Evaluation and Research of the U.S. FDA.

The dust mite allergens were Greer Laboratories, Allergenic Extract Standardized Mite, *Dermatophagoides farinae* (Der f) and/or *Dermatophagoides* pteronyssinus (Der p). The dust mite allergens are composed of extracts of whole mite bodies and fecal particles. The extract is standardized by a comparison of potency (measured by ELISA inhibition) against standardized mite extract references from the FDA.

The dog allergen was Greer Laboratories, Standardized Dog Hair Extract. The dog allergens are composed of dog hide, hair and dander standardized by comparing potency in dog allergen 1 (*Canis familiaris* 1) (Can f 1) units measured against a reference standard. The cockroach allergens were Greer Laboratories, Allergenic Extracts for Cockroaches, (Blatella germanica) (Bla g 1) composed of extracts of whole cockroach bodies. The extract is standardized by a comparison of potency against standardized cockroach references.

The clinical trial had the following parameters:

1. Each patient was exposed to 3 samples of the allergen to be tested.
2. One sample was the straight allergen extract.
3. The second sample was the allergen extract diluted with buffer (in the same amount as the aluminum sulfate solution).
4. The third sample was the allergen extract diluted by the addition of an 8.75% aluminum sulfate solution.
5. Skin evaluations ranged from negative (0) to positive (++++).
6. Thus, there were 5 gradations of skin wheal and flares.

The results for the reactions of the patients to the allergens can be seen in the attached FIGS. 1-4.

For the cat allergen the dilution effect diminished the skin reaction by a total of 16.3% while the sample treated with the novel composition provided by the invention diminished the skin reaction by a total of 72.0% (4.5 times the dilution effect).

For the dog allergen the dilution effect diminished the skin reaction by a total of 10.8% while the sample treated with the novel formulation diminished the skin reaction by a total of 70.2% (7 times the dilution effect).

For the dust mite fecal particle allergens the dilution effect diminished the skin reaction by a total of 6.9%. The sample treated with the novel formulation provided herein diminished the skin reaction by a total of 34.5% (5 times the dilution effect).

For the cockroach allergens the dilution effect diminished the skin reaction by a total of 21.2% while the aluminum sulfate treated sample diminished the skin reaction by a total of 72.7% (3.4 times the dilution effect).

The treatment of the various allergens with the composition provided by the invention diminished skin reaction in patients who were allergic to the specific cat, dog and cockroach allergens by almost 2 orders of magnitude. Reducing the allergens in contact with allergic patients will decrease cytokine release, which in turn reduces clinical symptoms without: (i) avoidance of the source of the allergen; (ii) pharmacotherapy; or (iii) immunotherapy.

The foregoing descriptions of novel and preferred embodiments of the invention have been presented for purposes of illustration and description. The descriptions are not intended to be exhaustive or to limit the invention to the precise form disclosed. Obvious modifications or variations are possible in light of the above testing. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the claims made in this application when interpreted in accordance with the breadth to which they are fairly, legally and equitably entitled.

What is claimed is:

1. A method for altering a protein in a subject animal's environment whereby the alteration of the protein mitigates an allergic reaction to the protein in the subject animal, comprising directly contacting the protein with a composition comprised of an effective amount of aluminum sulfate ($Al_2(SO_4)_3$), thereby altering the protein and mitigating an allergic reaction to the altered protein when the subject animal comes into contact with the altered protein.

2. The method of claim 1, wherein the aluminum sulfate of the composition is an acidic salt that is capable of forming an acidic solution in water with or without the presence of a suitable buffering agent.

3. The method of claim 1, wherein the effective amount is from between about 5 percent to about 10 percent aluminum sulfate.

4. The method of claim 3, wherein the effective amount is about 7 percent aluminum sulfate.

5. The method of claim 1, wherein the composition further comprises a suitable solvent and a suitable buffering agent.

6. The method of claim 5, wherein the suitable solvent is water and the suitable buffering agent is a citrate buffer.

7. The method of claim 1, wherein the subject animal is a human and the composition is formulated for contacting the protein on the coat or skin of a non-human animal, the formulation being selected from the group consisting of a powder, a gel, an ointment, a cream, a solution, a suspension, a sustained release preparation, a patch, a wet-wipe, a spray, and an aerosol.

8. The method of claim 1, wherein the protein structure is physically altered.

9. The method of claim 1, wherein the protein structure is chemically altered.

* * * * *